(12) United States Patent
Iaquaniello et al.

(10) Patent No.: US 9,102,532 B2
(45) Date of Patent: Aug. 11, 2015

(54) METHOD FOR PRODUCING SYNTHESIS GAS FOR METHANOL PRODUCTION

(71) Applicant: STAMICARBON B.V., Sittard (NL)

(72) Inventors: Gaetano Iaquaniello, Rome (IT); Elena Antonetti, Rome (IT); Palma Contaldo, Rome (IT)

(73) Assignee: STAMICARBON B.V., Sittard (NL)

( * ) Notice: Subject to any disclaimer, the term of this patent is extended or adjusted under 35 U.S.C. 154(b) by 0 days.

(21) Appl. No.: 14/354,536

(22) PCT Filed: Oct. 26, 2012

(86) PCT No.: PCT/NL2012/050748
§ 371 (c)(1),
(2) Date: Apr. 25, 2014

(87) PCT Pub. No.: WO2013/062415
PCT Pub. Date: May 2, 2013

(65) Prior Publication Data
US 2015/0087865 A1    Mar. 26, 2015

(30) Foreign Application Priority Data
Oct. 26, 2011    (EP) .................................... 11186764

(51) Int. Cl.
*C01B 3/26* (2006.01)
*C01B 3/30* (2006.01)
*C07C 29/151* (2006.01)
*C07C 29/00* (2006.01)

(52) U.S. Cl.
CPC ... *C01B 3/26* (2013.01); *C01B 3/30* (2013.01); *C07C 29/00* (2013.01); *C07C 29/1518* (2013.01); *C01B 2203/0261* (2013.01); *C01B 2203/0283* (2013.01); *C01B 2203/061* (2013.01)

(58) Field of Classification Search
None
See application file for complete search history.

(56) References Cited

U.S. PATENT DOCUMENTS

| 5,252,609 | A | 10/1993 | Pinto | |
|---|---|---|---|---|
| 7,485,767 | B2 * | 2/2009 | Lattner et al. | 585/639 |
| 2004/0101473 | A1 * | 5/2004 | Wang et al. | 423/651 |
| 2004/0171701 | A1 * | 9/2004 | Shaw | 518/700 |
| 2008/0275143 | A1 | 11/2008 | Malhotra et al. | |

FOREIGN PATENT DOCUMENTS

| EP | 640559 | 3/1995 | |
|---|---|---|---|
| EP | 1 219 566 | 7/2002 | |
| EP | 2 199 254 | 6/2010 | |
| WO | WO-00/00426 | 1/2000 | |
| WO | WO-01/32556 | 5/2001 | |
| WO | WO-01/36323 | 5/2001 | |
| WO | WO-2006/117499 | 11/2006 | |
| WO | WO 2011/018233 A1 * | 2/2011 | ................ C01B 3/38 |
| WO | WO-2011/072877 | 6/2011 | |

OTHER PUBLICATIONS

Basini, "Fuel rich catalytic combustion: Principles and technological developments in short contact time (SCT) catalytic processes," Catalysis Today (2006) 117:384-393.
International Search Report for PCT/NL2012/050748, mailed Feb. 18, 2013, 3 pages.
Reimert et al., "Gas Production, 5. Examples of Complex Gas Production Plants," in: Ullmann's Encyclopedia of Industrial Chemistry, (2011) Wiley-VCH Verlag GmbH & Co., Weinheim, Germany, p. 557.
Basini et al., "Catalytic partial oxidation of natural gas at elevated pressure and low residence time," Catalysis Today (2001) 64(1-2):9-20.
Hickman and Schmidt, "Production of syngas by direct catalytic oxidation of methane," Science (1993) 259(5093):343-346.
Hickman and Schmidt, "Synthesis gas formation by direct oxidation of methane over Pt monoliths," J Catalysis (1992) 138(1):267-282.

* cited by examiner

*Primary Examiner* — Brian J Davis
(74) *Attorney, Agent, or Firm* — Morrison & Foerster LLP

(57) ABSTRACT

Method for producing synthesis gas for methanol production The present invention relates to a method for producing synthesis gas from a hydrocarbon containing feed, which synthesis gas is particularly suitable for subsequent use in methanol production. In this method, a feed (100) is divided into two streams, wherein one stream is subjected to catalytic partial oxidation (CPO) (2) and the other stream is subjected to steam reforming (5) followed by a water gas shift reaction (51). The two streams are then recombined and can be used further in methanol synthesis (6). The recombined stream preferably has an R ratio, being a molar ratio $(H_2-CO_2)/(CO+CO_2)$, in the range of 1.9-2.2 and preferably about 2. The invention further relates to a method for producing methanol from a hydrocarbon containing feed, wherein first synthesis gas is obtained according to the method of the invention, which synthesis gas is further used to produce methanol. Also, the invention relates to a method of adapting an existing methanol plant to the methanol production process of the invention.

15 Claims, 2 Drawing Sheets

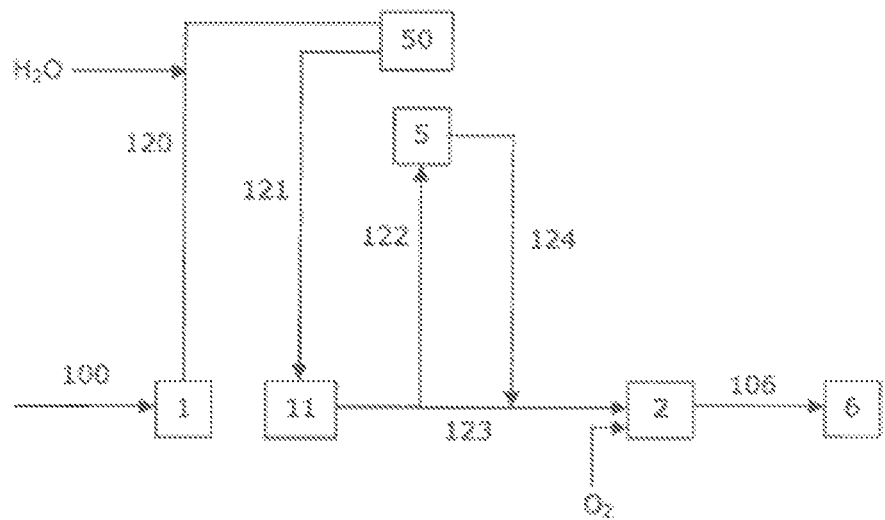
Figure 1 -- Prior Art --
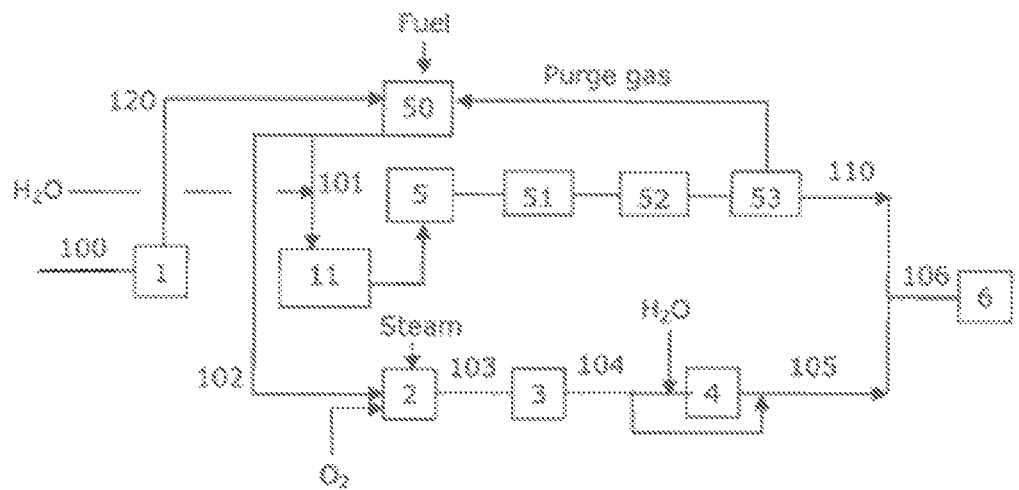
Figure 2

METHOD FOR PRODUCING SYNTHESIS GAS FOR METHANOL PRODUCTION

CROSS-REFERENCE TO RELATED APPLICATIONS

This application is the national phase of PCT application PCT/NL2012/050748 having an international filing date of 26 Oct. 2012, which claims benefit of European patent application No. 11186764.4 filed 26 Oct. 2011. The contents of the above patent applications are incorporated by reference herein in their entirety.

FIELD OF THE INVENTION

The present invention relates to the field of synthesis gas production from light hydrocarbons such as natural gas. In particular, the present invention relates to the production of synthesis gas particularly suitable for methanol production.

BACKGROUND OF THE INVENTION

Commercial methanol plants produce methanol in several steps, usually including synthesis gas preparation (reforming), methanol synthesis and methanol purification. Since these steps are conducted in separate process sections, the technology for each section can be selected and optimised independently. The usual criteria for the selection of technology are capital cost and plant efficiency. The preparation of synthesis gas and compression typically accounts for about 60% of the investment, and almost all energy is consumed in this process section. Therefore, the technology to produce synthesis gas is of major importance, regardless of the site.

The synthesis gas for the production of methanol is usually obtained by subjecting a desulfurized hydrocarbon feed to steam reforming (SR) at a temperature from 800 to 950° C. in the presence of a fixed bed of catalyst, typically containing nickel. The resulting synthesis gas is cooled and compressed to be used further in the methanol process. However, the synthesis gas obtained in steam reforming is usually characterized by a too low carbon/hydrogen ratio compared to a stoichiometric composition optimal for methanol synthesis. As a result, the methanol synthesis reactor typically operates at a large hydrogen excess which results in an overall low plant efficiency.

To adjust the composition of the synthesis gas used for methanol production, a combination of technologies can be used. A known method for methanol production also known as Combined Reforming Technology (CRT) is described in EP 0233076. Herein, a hydrocarbon feed is split into two feedstock fractions, of which one fraction is subjected to a primary steam reforming and is then combined with the second feedstock fraction. The resulting mixture is reacted with an oxygen containing gas in a secondary reforming reactor. The resulting raw synthesis gas is mixed with a hydrogen-rich stream obtained from the purge gas from a methanol synthesis loop, which final mixture is then fed to the synthesis loop for methanol production. In order to achieve a stoichiometric ratio of hydrogen to carbon oxides, up to 50-60% of the entire feed needs to be subjected to steam reforming. This makes the steam reforming section of a methanol plant a considerable fraction of the investment of the entire plant. In addition, high steam reforming duty is also associated with a significant fuel consumption by external burners in order to maintain required high temperatures during steam reforming. This, in turn, leads to high $CO_2$ emissions into the atmosphere.

It is therefore desired to provide a method for producing synthesis gas for methanol production, which process would be substantially devoid of the above disadvantages. Particularly, it is desired to have a process with a reduced fuel consumption and a reduced $CO_2$ emission while producing synthesis gas having an optimal components ratio for methanol production.

SUMMARY OF THE INVENTION

In order to better address one or more of the foregoing desires, the invention presents, in one aspect, a method for producing synthesis gas from a hydrocarbon containing feed, comprising the steps of:
(i) dividing a hydrocarbon containing feed into first and second hydrocarbon feeds,
(ii) subjecting said first hydrocarbon feed to catalytic partial oxidation (CPO) yielding a first reaction product mixture comprising $H_2$, CO and $CO_2$,
(iii) subjecting said second hydrocarbon feed to steam reforming followed by a water gas shift reaction to yield a second reaction product mixture, and
(iv) combining said first and said second reaction product mixtures to yield a synthesis gas for methanol synthesis, wherein the first reaction product mixture comprises less than 10% $CO_2$ on dry basis.

The invention, in another aspect, is a method for producing methanol from a hydrocarbon containing feed comprising the steps according to claim 1 to obtain a synthesis gas, and using said synthesis gas to produce methanol.

In a further aspect, the invention provides a method for adapting an existing methanol plant comprising a steam reforming unit to the methanol production process according to the invention, said method comprising adding a CPO unit in parallel with the steam reforming unit, to the existing methanol plant.

BRIEF DESCRIPTION OF THE DRAWINGS

FIG. 1 shows a block scheme of a conventional combined reformer with a pre-reforming section.

FIG. 2 shows a block scheme for the production of synthesis gas according to an embodiment of the present invention, with a pre-reforming section only for a SR feed.

DETAILED DESCRIPTION OF THE INVENTION

Figure 3:
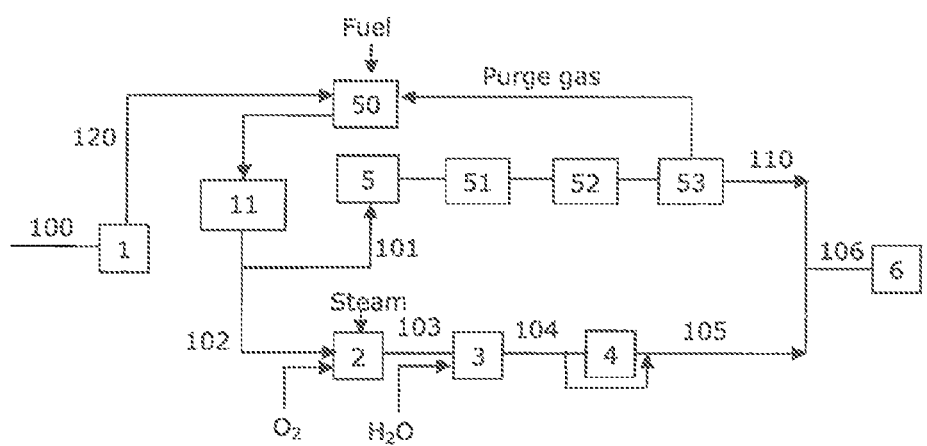
FIG. 3 shows a block scheme of an embodiment of the present invention with a common pre-reforming section.

In general, according to the present invention, a hydrocarbon containing feed is divided into two feeds that are treated separately. The resulting feeds are further recombined to obtain synthesis gas particularly suitable for methanol production. As used herein, a synthesis gas suitable for methanol production means that the synthesis gas has a certain ratio of components, especially of hydrogen and carbon oxides, which is optimal for methanol synthesis. In particular, methanol synthesis gas can be characterised by a molar ratio $(H_2-CO_2)/(CO+CO_2)$, referred to herein as an R ratio. An R ratio equal to 2 defines a stoichiometric synthesis gas for formation of methanol. The synthesis gas obtained according to the method of the present invention has preferably, an R ratio in the range of 1.90-2.20, more preferably 1.95-2.05.

Other important properties of the synthesis gas are the CO to $CO_2$ ratio and the concentration of inerts. A high CO to $CO_2$ ratio will increase the reaction rate and conversion and also decrease the water formation, which in turn reduces the catalyst deactivation rate. A high concentration of inerts will lower the partial pressure of the active reactants. Inerts in the methanol synthesis are typically methane, argon and nitrogen.

According to the invention, a hydrocarbon containing feed is divided into first and second hydrocarbon feeds, of which the first is subjected to catalytic partial oxidation and the second to steam reforming. Any hydrocarbon containing feed suitable for steam reforming can be used. Preferably, the feed contains light hydrocarbons such as $C_{1-4}$ alkanes, e.g. methane, ethane, etc. More preferably, the feed contains methane or a gas containing substantial amounts of methane, e.g. natural gas. It is preferred to use a desulfurized feed. Therefore, if needed, the hydrocarbon feed can be subjected to a desulfurization step prior to dividing into two feeds. Under hydrocarbon feed any feed containing at least one hydrocarbon is meant.

The ratio of dividing the feed into two feeds is dependent on the feed composition and on a desired composition of the final synthesis gas. The desired composition is determined by the final application of the synthesis gas, e.g. methanol production in a particular case. In general, the second hydrocarbon feed, which will be supplied to a steam reformer, constitutes preferably less than a half of the whole hydrocarbon feed in volume, and preferably 5 to 30 vol. % of the total hydrocarbon containing feed is divided as the second hydrocarbon feed. In an alternative embodiment, the volume ratio of the first hydrocarbon feed to the second hydrocarbon feed is preferably from 20:1 to 2:1, and more preferably from 15:1 to 5:1.

When the synthesis gas is used for methanol production, the second feed is preferably 5-15 vol. % of the whole hydrocarbon feed. Best results are achieved when the second feed is about 10 vol. % of the whole hydrocarbon feed. Before dividing, the hydrocarbon feed, or part of it, can be subjected to pre-reforming.

The first hydrocarbon feed is subjected to catalytic partial oxidation (CPO). This typically involves a reaction of hydrocarbons with steam and oxygen in the presence of a catalyst. In case of natural gas or other methane containing feed, the reaction can be represented as follows:

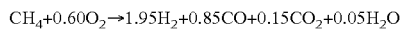

$$CH_4 + 0.60 O_2 \rightarrow 1.95 H_2 + 0.85 CO + 0.15 CO_2 + 0.05 H_2O$$

In this reaction, the R ratio of the product is typically 1.87. The reaction is typically performed at a temperature of 800-900° C. in the presence of a metal catalyst. The catalytic metal is preferably a Group VIII noble metal, e.g., platinum, iridium, rhodium, osmium, ruthenium, although nickel may also be used as the catalytic metal. The oxygen used in the catalytic partial oxidation process may be pure or substantially pure oxygen or an oxygen containing gas, e.g., air, or a mixture of oxygen with an inert gas. Substantially pure oxygen (that is, containing more than 99% oxygen) is preferred, and pure oxygen containing more than 99.9% oxygen is still more preferred.

The feed stream supplied to the CPO reactor is preferably preheated to a temperature of 200-500° C., preferably 350-450° C. and in particular about 400° C. At these temperatures, the supply of oxygen to the CPO reactor is minimized. This also reduces the costs for the air separation unit (ASU), in case the latter is used to obtain oxygen for the CPO reaction. Preheating can conveniently be done in a convection section of a steam reformer. The hydrocarbon containing feed and the oxygen can be in various ratios in the feed gas mixture. The precise mixture introduced into the reaction zone depends on the particular hydrocarbons used and the amount of oxygen necessary to conduct the partial oxidation reaction. Operable ratios can be easily determined by one skilled in the art. Usually, the $O_2/C$ (Oxygen to Carbon) ratio is around 0.4-0.6, preferably 0.5.

The term CPO (also referred to as SCT-CPO) is known to the skilled person. SCT-CPO refers to Short Contact Time Catalytic Partial Oxidation. The CPO reaction takes place in a reactor under the influence of a catalyst at residence times between $10^{-2}$ to $10^{-4}$ and with typical catalyst surface contact times around $10^{-6}$ s$^{-1}$. These contact time correspond to typical space velocities of 100,000 to 250,000 hr$^{-1}$, preferably 100,000 to 200,000 hr$^{-1}$. Catalysts employed for SCT-CPO comprise Ni, Pd, Pt, Rh, or Ru. The reaction takes place at catalyst surface temperatures above 950° C., preferably above 1000° C. By employing said short contact times and high catalyst surface temperatures the formation of CO is highly favoured and the formation of carbon or $CO_2$ is suppressed. This leads to a highly favourable synthesis gas composition. A reference to CPO is (a) L. Basini, Catalysis Today 117 (2006) 384-393. Other references include (b) L. Basini, K. Aasberg-Petersen, A. Guarinoni, M. Oestberg, Catalysis Today (2001) 64, 9-20 "Catalytic Partial Oxidation of Natural Gas at Elevated Pressure and Low Residence Time"; (c) H. Hickman, L. D. Schmidt, J. Catal. 138 (1992) 267; (d) D. Hichman, L. D. Schmidt Science, 259 (1993) 343; (e) L. Basini, G. Donati WO 97/37929; (f) Sanfilippo, Domenico; Basini, Luca; Marchionna, Mario; EP-640559; (g) D. Schaddenhorst, R. J. Schoonebeek; WO 00/00426; (h) K. L. Hohn, L. D. Schmidt, S. Reyes, J. S. Freeley, WO 01/32556; (i) A. M. Gaffney, R. Songer, R. Ostwald, D. Corbin, WO 01/36323. As a result of the SCT-CPO reaction, a first reaction product mixture is obtained comprising hydrogen ($H_2$), carbon monoxide (CO) and carbon dioxide ($CO_2$). In a preferred embodiment, this reaction product mixture contains less carbon dioxide than in a conventional CRT process. This is particularly advantageous in methanol plants, which require a $CO_2$ content as low as possible. Preferably, the first reaction product mixture comprises less than 10% $CO_2$ dry basis, more preferably less than 6% $CO_2$ dry basis. The low carbon dioxide content contributes to the optimized R ratio of the end product synthesis gas, which R ratio cannot be obtained with conventional PDX or conventional CPO methods.

In a preferred embodiment, part of the CO is converted into $CO_2$ in the presence of steam in a water gas shift (WGS) reactor, reducing thereby the $CO/CO_2$ ratio in the reaction product mixture preferably to a value from 3 to 10, more preferably to a value from 6 to 7. The $CO/CO_2$ ratio may further be adjusted by modifying the amount of gas flowing through a by-pass around the WGS reactor, if desired.

The second hydrocarbon feed is subjected to steam reforming (SR) in a steam reformer. Before steam reforming, the feed can be subjected to pre-reforming. In a pre-reformer, higher hydrocarbons (higher than $C_1$) are converted into methane, which makes the feed more uniform and also reduces the SR duty. The conversion reaction in the pre-reformer is particularly effective when the feed is introduced into the pre-reformer at a temperature of 250-600° C., preferably 450-550° C. and in particular about 500° C. Preheating of the pre-reforming feed can conveniently be done in a convection section of the SR section. An adiabatic steam reforming can be used as pre-reforming. In the pre-reforming the steam-to-carbon molar ratio is preferably from 1.5 to 2, more preferably about 1.6-1.7. Besides pre-reforming of the second hydrocarbon feed only, it is also advantageous to subject the entire feed or a part of it, before splitting, to pre-reforming. In case all the feed is treated in a pre-reforming, preferably in an adiabatic steam reforming, the oxygen consumption is minimised.

The steam reforming is preferably followed by a water gas shift reaction to convert CO to $CO_2$ and additional $H_2$. This yields a second reaction product mixture comprising hydrogen and carbon dioxide. The product mixture can also be purified to separate $CO_2$ and obtain a hydrogen-rich stream. In a preferred embodiment, the carbon dioxide is removed from the second reaction product mixture by pressure swing adsorption (PSA).

The second reaction product mixture is then combined with the first reaction product mixture. In this way, the R ratio is raised to above 1.9, and preferably to about 2.

By applying the method of the invention, the duty of a steam reforming section can be reduced to a value between 30 to 70% and preferably 40-50% of that in the conventional Combined Reforming. In addition, the $CO_2$ emissions are reduced at least by 50% compared with the conventional technology.

The present invention provides a method to operate the steam reformer more efficiently in a process for making synthesis gas for making methanol. In the processes of the prior art, very large steam reformer units are needed which requires a very costly investment. Furthermore these units are typically operated with an excess of hydrogen.

The present invention leads to an optimized process with a high yield of methanol with the minimum energy usage in steam reforming. Another advantage of the process is that typically the WGS reaction and the $CO_2$ removal, e.g. by PSA, only need to be applied to the second reaction mixture.

The resulting synthesis gas has the R ratio, being molar ratio $(H_2-CO_2)/(CO+CO_2)$, that is particularly suitable for methanol production. In particular, the R ratio is in the range of 1.90-2.20, more preferably 1.95-2.05. It should be noted that parameter R is defined such that the R ratio does not change during the WGS step. During the WGS reaction CO is converted into $CO_2$ with formation of $H_2$, but the R ratio stays the same. This can be explained by that in the WGS reaction for every mole of CO that is converted to $CO_2$ one mole of $H_2$ is produced. The difference $(H_2-CO_2)$ thus stays the same as well as the sum $(CO+CO_2)$. The R ratio is thus only influenced by the mixing of the first and second reaction mixture.

In another aspect, the present invention relates to a method for producing methanol from a hydrocarbon containing feed. The method comprises the steps previously described to obtain a synthesis gas, which synthesis gas is then used to produce methanol. Any suitable method to produce methanol from synthesis gas can be used. Typically, carbon oxides and hydrogen from the synthesis gas react on a catalyst to produce methanol. The catalyst for this reaction usually contains copper and zinc.

In yet a further aspect, the present invention relates to a method for adapting an existing methanol plant comprising a steam reforming unit to the methanol production process according to the present invention, said method comprising adding a CPO unit in parallel with the steam reforming unit, to the existing methanol plant. Under CPO unit also SCT-CPO units are meant, as described above. The steam reforming unit preferably comprises a steam reformer and a shift reactor for performing the water-gas shift reaction. The CPO unit is installed in an existing methanol plant in such a way that makes it possible to conduct the methanol production process as described above. In particular, the CPO unit is installed in parallel with the SR unit, which in turn may comprise a steam reformer and a shift (WGS) reactor. One of the advantages of the addition of the SCT-CPO is increased total methanol capacity. Another advantage is improved energy efficiency of the steam reformer because no extra $H_2$ needs to be produced. It should be noted that the typical size and footprint of a CPO unit is significantly smaller than a typical SR unit. In case of a desired capacity increase of a methanol plant, but a limited available space to expand the SR unit, there may be space to place a CPO unit. The present invention will further be described with respect to particular embodiments and with reference to certain drawings but the invention is not limited thereto but only by the claims. Any reference signs in the claims shall not be construed as limiting the scope. If not specifically indicated, all percentages for gases are given by volume. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

FIG. 1 illustrates a known combined technology process. In this process, a natural gas feed 100 is desulfurized in a hydrodesulfurization (HDS) reactor 1. A desulfurized feed 120 is then subjected to pre-heating in a convection section 50 of a steam reformer (SR). Preheated stream 121 is added with steam and is further supplied to a pre-reformer 11, whereafter the stream is split into two streams, 122 and 123. Stream 122 is supplied to the steam reformer 5, in which natural gas together with steam is catalytically converted to a synthesis gas 124. Stream 123 is mixed with synthesis gas 124 and both are fed into an autothermal reformer (ATR) 2. In the ATR, the mixed gas stream together with oxygen is reformed to a synthesis gas 106, which has a proper composition to be used (after compression) for methanol synthesis in a synthesis reactor 6.

In FIG. 2, an embodiment according to the present invention is shown. A hydrocarbon feed 100, particularly natural gas, is desulfurized in a HDS reactor 1. The feed stream is preheated in a convection section 50 of a steam reformer, and then split in two streams, 101 and 102. Stream 101 is added with steam, subjected to pre-reforming in a pre-reforming section 11 and then supplied to a SR section, which contains a SR reactor 5 together with a HT shift reactor 51, followed by a pressure-swing adsorption (PSA) unit 53. Optionally, $CO_2$ can be removed in unit 52 preceding (or replacing) the PSA unit 53; $CO_2$ removal is obtained through a solvent wash system, such as amine, selexol or other known solvents. After PSA, a pure $H_2$ stream 110 is obtained.

Stream 102 together with a super heated steam is mixed with preheated oxygen and enters the catalyst bed of the CPO reactor 2. The produced gas 103, cooled in a process gas boiler 3 to yield stream 104, which is split thereafter into two streams, one of which is introduced into a CO shift reactor 4 and the other by-passes it. Before being introduced into the CO shift reactor, further steam is added to the first stream. The streams are recombined to yield stream 105, which stream is characterized by the same R ratio as stream 103 but has a decreased $CO/CO_2$ ratio, which is aligned to about 2.6. Streams 105 and 110 are mixed to obtain stream 106 which is supplied, after compression, to a methanol synthesis reactor 5. The ratio $H_2/CO$ of stream 106 is about 3 and the R ratio is about 2.

The ratio of splitting of the feed into streams 101 and 102 depends on the feed composition and $H_2/CO$ ratio. For methanol plants, the R is 2 and the $H_2/CO$ ratio is about 3:1. For this purpose, feed stream 101 constitutes preferably about 5-30 vol. % of stream 100. If natural gas is applied, this stream is preferably less than 10% of the entire feed stream 100. In other applications, however, up to 30% of the feed can be branched off as stream 101.

FIG. 3 shows another preferred embodiment of the present invention. After a desulfurization step of a feed stream 100, a feed stream 120 is obtained which is heated in a convection section 50 of a reformer to about 500° C. and is supplied to a pre-reformer 11. Downstream of the pre-reformer 11, the stream is split into two streams, supplied to CPO and SR sections. The remaining part of this scheme corresponds to that of FIG. 2, so that reference can be made to the above explanations. Accordingly, identical components of the plant are provided with the same reference numerals. In this embodiment, heavy natural gas is processed using heat provided by the convection section 50 of the SR, which leads to the reduction of oxygen consumption and the reduction of the overall size of the SR section. In this embodiment it is also possible to subject only a part of the CPO feed to pre-reforming.

In Table 1, the process characteristics for several exemplary embodiments of the invention are shown, together with a reference example based on a combined SR/ATR technology. The WGS ratio is the ratio between the stream sent to the shift reactor and the total effluent from the CPO.

TABLE 1

|  | Ref. case | Case 1 | Case 2 | Case 3 | Case 4 |
| --- | --- | --- | --- | --- | --- |
| Feed + Fuel (wt) | 100 | 97 | 98 | 97 | 94 |
| Oxygen | 100 | 127 | 119 | 127 | 118 |
| Reformer Duty | 100 | 39 | 64 | 40 | 63 |
| SR/ATR streams ratio | 60/100 | — | — | — | — |
| SR/CPO streams ratio | — | 9/91 | 15/85 | 9/91 | 15/85 |
| Steam/C to CPO | — | 0.6 | 0.6 | 1.34 | 0.4 |
| CO/CO$_2$ outlet CPO | — | 6 | 5 | 2.6 | 6 |
| WGS ratio | — | 0.36 | 0.31 | — | 0.48 |

Case 1 is an embodiment according to the present invention, wherein pre-reforming of steam reforming feed and no recycling of a product purge gas from PSA to the CPO reactor are performed.

Case 2 is an embodiment according to the present invention, wherein pre-reforming of steam reforming feed and recycling about 50% of product purge gas from PSA to the CPO reactor are performed.

Case 3 is an embodiment according to the present invention, wherein pre-reforming of steam reforming feed and pre-reforming of 40% of CPO feed are performed Case 4 is similar to case 1 but has a steam-to-carbon molar ratio of 0.4 of the feed supplied to the CPO reactor.

In all presented cases the steam-to-carbon molar ratio of a feed supplied to the pre-reformer is 1.5, while the steam-to-carbon molar ratio supplied to the steam reformer is 3.

Table 1 demonstrates the reduction of feed and fuel consumption and of the reformer duty for several embodiments of the present invention compared to a known combined reforming technology. The reduction of the reformer duty translates, in turn, into a considerable reduction of the capital costs of the plant and reduced CO$_2$ emission.

The invention claimed is:

1. Method for producing synthesis gas from a hydrocarbon containing feed, comprising the steps of:
   (i) dividing a hydrocarbon containing feed into first and second hydrocarbon feeds,
   (ii) subjecting said first hydrocarbon feed to catalytic partial oxidation (CPO) yielding a first reaction product mixture comprising H$_2$, CO and CO$_2$,
   (iii) subjecting said second hydrocarbon feed to steam reforming followed by a water gas shift reaction to yield a second reaction product mixture, and
   (iv) combining said first and said second reaction product mixtures to yield a synthesis gas for methanol synthesis, wherein the first reaction product mixture comprises less than 10% CO$_2$ on dry basis.

2. The method according to claim 1, wherein the synthesis gas has an R ratio which is the molar ratio (H$_2$–CO$_2$)/(CO+CO$_2$), in the range from 1.90 to 2.20.

3. The method according to claim 1, wherein in step (i) 5 to 30 vol. % of the hydrocarbon containing feed is divided as the second hydrocarbon feed.

4. The method according to claim 1, wherein in step (iii) the second reaction product mixture is subjected to pressure swing adsorption.

5. The method according to claim 1, wherein at least a part of the hydrocarbon feed is subjected to pre-reforming before step (i).

6. The method according to claim 1, wherein the second hydrocarbon feed is subjected to pre-reforming.

7. The method according to claim 5, wherein the pre-reforming temperature is from 250 to 600° C.

8. The method according to claim 1, wherein the first hydrocarbon feed in step (ii) is preheated to a temperature from 200 to 500° C.

9. The method according to claim 1, wherein the first reaction product mixture comprises less than 6% CO$_2$ by volume on dry basis.

10. The method according to claim 1, wherein the first reaction product mixture has a CO/CO$_2$ ratio by volume from 3 to 10.

11. Method for producing methanol from a hydrocarbon containing feed comprising performing the steps according to claim 1 to obtain a synthesis gas, and converting said synthesis gas to produce methanol.

12. Method for adapting an existing methanol plant comprising a steam reforming unit to the methanol production process according to claim 11, said method comprising adding a CPO unit in parallel with the steam reforming unit to the existing methanol plant.

13. The method according to claim 12, wherein the steam reforming unit comprises a steam reformer and a shift reactor for performing a water-gas shift reaction.

14. The method according to claim 7, wherein the pre-reforming temperature is from 450 to 550° C.

15. The method according to claim 8, wherein the first hydrocarbon feed in step (ii) is preheated to a temperature from 350 to 450° C.

* * * * *

UNITED STATES PATENT AND TRADEMARK OFFICE
CERTIFICATE OF CORRECTION

| | | |
|---|---|---|
| PATENT NO. | : 9,102,532 B2 | Page 1 of 1 |
| APPLICATION NO. | : 14/354536 | |
| DATED | : August 11, 2015 | |
| INVENTOR(S) | : Iaquaniello et al. | |

It is certified that error appears in the above-identified patent and that said Letters Patent is hereby corrected as shown below:

On the title page, item (73)

DELETE "Stamicarbon B.V."

INSERT --Stamicarbon B.V. Acting Under the Name of MT Innovation Center--

Signed and Sealed this
Twelfth Day of January, 2016

Michelle K. Lee
*Director of the United States Patent and Trademark Office*